United States Patent [19]

Valentine

[11] Patent Number: 4,684,534

[45] Date of Patent: Aug. 4, 1987

[54] QUICK-LIQUIFYING, CHEWABLE TABLET

[75] Inventor: William Valentine, Rocky Hill, Conn.

[73] Assignee: Dynagram Corporation of America, Lawrenceville, Ga.

[21] Appl. No.: 702,818

[22] Filed: Feb. 19, 1985

[51] Int. Cl.[4] .................. A61K 9/00; A61K 15/00; A61K 21/00

[52] U.S. Cl. ..................... 427/3; 424/447; 424/448; 514/777; 514/960

[58] Field of Search .............. 514/960, 777; 424/14, 424/35; 427/3

[56] References Cited

U.S. PATENT DOCUMENTS

| | | | |
|---|---|---|---|
| 2,421,801 | 6/1947 | Miller | 427/3 |
| 2,813,123 | 11/1957 | Valentine et al. | 514/625 |
| 2,830,010 | 4/1958 | Valentine et al. | 424/37 |
| 2,879,161 | 3/1959 | Valentine et al. | 426/648 |
| 2,946,724 | 7/1960 | Valentine | 424/89 |
| 2,996,431 | 8/1961 | Barry | 427/3 |
| 3,055,804 | 9/1962 | Valentine | 424/160 |
| 3,085,944 | 4/1983 | Valentine | 424/96 |
| 3,305,447 | 2/1967 | Reimers et al. | 127/30 |
| 3,365,331 | 1/1968 | Miller et al. | 127/30 |
| 3,540,927 | 11/1970 | Miimi et al. | 127/30 |
| 3,619,292 | 11/1971 | Broulliard et al. | 127/29 |
| 3,619,293 | 11/1971 | Niimi | 127/30 |
| 3,619,294 | 11/1971 | Black et al. | 127/30 |
| 3,622,677 | 11/1971 | Short et al. | 514/778 |
| 3,627,583 | 12/1971 | Troy et al. | 127/29 |
| 3,639,168 | 2/1972 | Monti et al. | 127/29 |
| 3,639,169 | 2/1972 | Broeg et al. | 127/29 |
| 3,642,535 | 2/1972 | Graham et al. | 127/29 |
| 3,674,555 | 7/1972 | Meyer et al. | 127/29 |
| 3,725,556 | 4/1973 | Hanssen et al. | 514/770 |
| 3,849,194 | 11/1974 | Armbruster et al. | 127/29 |
| 3,873,694 | 3/1975 | Kanig | 424/127 |
| 4,013,775 | 3/1977 | Nelson et al. | 426/285 |
| 4,349,542 | 9/1982 | Staniforth | 424/153 |
| 4,447,532 | 5/1984 | Coker et al. | 435/99 |
| 4,517,179 | 5/1985 | Raghunathan | 514/960 |

FOREIGN PATENT DOCUMENTS

| | | |
|---|---|---|
| 740236 | 10/1969 | Belgium . |
| 1063535 | 3/1967 | United Kingdom . |
| 1286275 | 8/1972 | United Kingdom . |

Primary Examiner—Ronald W. Griffin
Attorney, Agent, or Firm—Amster, Rothstein & Ebenstein

[57] ABSTRACT

This application discloses tablets having a harder outer shell which inhibits penetration of liquid into the interior of the tablet, and a softer interior which quickly liquifies when the tablet and shell are broken into pieces and contacted by the liquid. The tablet has particular utility as a chewable tablet which resists absorption of moisture but which quickly liquifies and melts in the mouth within seconds after mastication, even if the tablet contains considerable amounts of active ingredients that do not dissolve well or at all in the mouth. Also disclosed are agglomerates from which the tablets are directly compressed, and processes for making the agglomerates and tablets. The tablets contain increased quantities of active ingredients of up to about 75% by weight. The excipient or base material of the tablet is made from carbohydrates including dextrose, dextrose monohydrate, maltodextrin, fructose, sucrose, lactose, maltose and xylose held together by small quantities of a carbohydrate binder such as maltodextrin. Tablets according to the invention can contain active ingredients such a pharmaceuticals (e.g., antacids, analgesics, cough medicine, drugs, etc.) breath sweeteners, vitamins and dietary supplements, to name a few.

64 Claims, 2 Drawing Figures

QUICK-LIQUIFYING, CHEWABLE TABLET

BACKGROUND OF THE INVENTION

The present invention relates generally to tablets which quickly liquify upon being broken and subjected to a liquid, and to agglomerates from which such tablets are made, and to processes for making the agglomerates and tablets. The present invention more particularly relates to tablets which quickly liquify in the mouth when chewed and to processes for their manufacture.

A need has long existed in the pharmaceutical industry for an oral dosage form which stores well, is convenient and pleasant to take, efficacious, fast acting, and portable. Liquids are desirable because the active ingredients are already liquified, they can be swallowed easily, and, in the case of preparations such as antacids and cough medicines, soothe the throat and esophagus on the way to the stomach. However, liquids are not easily portable, often require refrigeration and require some utensil to measure and administer the dosage. Solid dosage forms, such as tablets, usually are portable and easily stored, but a liquid such as water is usually required as an aid in swallowing, and they are generally not as fast acting or as efficacious as liquids. While some tablets, such as antacid tablets, can be chewed to begin dissolution which is completed in the stomach, they do not liquify in the mouth and are swallowed as gritty particles.

Antacid preparations are sold in both liquid and solid form to treat a wide range of disorders such as simple upset stomach, heartburn, acid or nervous indigestion and ulcers. Liquids, while being generally preferred because they are perceived to be faster acting and better tasting, and because they react more quickly with excess gastric acid and immediately soothe esophagal heartburn or nervous indigestion, suffer from the previous mentioned drawbacks. Currently available solid antacid tablets are quite portable and convenient to take, but do not liquify well in the mouth, are not perceived to be as effective as the liquids and do not soothe esophagal heartburn or nervous indigestion on the way to the stomach. Moreover, solid antacid tablets are not particularly good tasting and do not sweeten the breath, which would be extremely desirable for those who suffer from esophagal reflux or sour breath. In addition, solid antacid tablets when chewed produce gritty and chalky particles which are unpleasant tasting and quite unpallatable.

OBJECTS AND SUMMARY OF THE INVENTION

It is an object of the present invention to provide a tablet which stores well and liquifies quickly when used, particularly a tablet which liquifies quickly in the mouth upon chewing and is pleasant tasting.

It is another object of the present invention to provide a tablet by direct compression which includes a substantial quantity of an active ingredient, particularly an active ingredient which in its raw material form is a powder that can not be compacted into a cohesive tablet easily or at all.

It is still another object of the present invention to provide agglomerates from which such tablets can be directly compressed and to provide processes for making such agglomerates.

A tablet according to the present invention is directly compressed from specially formed high surface area, carbohydrate-based agglomerate particles and comprises a relatively soft, quick-liquifying interior and a relatively hard, protective outer shell which resists liquification even though it is formed from the same agglomerate particles which form the tablet interior. At least some of the ingredients of the agglomerate particles in the interior of the tablet quickly dissolve or partially dissolve when the tablet is broken into pieces contacted with small amounts of a liquid, particularly water and/or saliva, as during mastication, for example, and any remaining ingredients which do not dissolve in the liquid become dispersed in the liquid and dissolved ingredients, so that the resulting liquid is smooth and essentially without perceivable grit.

The agglomerate particles which form the tablet interior are rapidly liquified when the tablet is broken up, as for example during mastication, and the particles are contacted with small amounts of a liquid including, for example, the saliva normally available in the mouth. However, the relatively hard outer shell resists liquification until it is broken, for example, by chewing. Accordingly, the overall tablet structure is such that the tablet is not only stable and easily portable, thereby providing a unit dose in the most convenient form, but is also readily liquified and melts in the saliva of the mouth during mastication without requiring water or some other liquid, so that the tablet provides all of the benefits normally associated only with liquid dosage forms.

The carbohydrate-based agglomerates comprise carbohydrate particles selected from the group consisting of dextrose, dextrose monohydrate, maltodextrine, fructose, sucrose, lactose, maltose and xylose; and a water-soluble binder selected from the group consisting of maltodextrine, corn syrup solids, dextrose, sucrose, polyvinylpyrollidone and cooked starch paste. The quantity of water-soluble binder is somewhat critical and should be in the range of from about 1 percent to about 10 percent by weight of the agglomerate (without active ingredient), and preferably from about 1 percent to about 5 percent, with the carbohydrate-based particles comprising from about 90 percent to about 99 percent by weight of the agglomerate (without active ingredient). The particle size of the materials used to make the agglomerates and the tablet have been found to be important, as described below.

While not wishing to be limited to any particular theory, it is believed that the agglomerates from which the tablets are made have an open pore or duct-like structure and a resulting large surface area to volume ratio which causes the particles to readily dissolve on contact with small amounts of any liquid, including saliva, in which the agglomerate is at least partially soluble. The pores or ducts of the agglomerate structure which are believed to provide the large surface area are capable of entraining relatively large quantities of an active ingredient. The agglomerate structure is thus honeycomb in nature and resembles that of zeolite. By virtue of this structure, the large surface area of the agglomerate becomes accessible for contact by a liquid in which at least the carbohydrate binder dissolves so that the agglomerate particles quickly liquify and entrain or dissolve the active ingredient depending on its solubility. This agglomerate structure is believed not to be substantially destroyed in the interior of the tablet by compression, while the relatively hard outer shell of the tablet, although made from the same material as the interior of the tablet, appears to be formed from partial destruction or blockage of the agglomerate pore structure at the tablet surface as a result of the compressive forces which are applied by the smooth walls of the mold cavity during formation of the tablet. The shell thus acts as a protective mechanism which not only mechanically assists in holding the tablet together but also blocks the open pore structure in the interior of the tablet from the exterior of the tablet and thereby inhibits penetration of a liquid solvent into the interior of the tablet. It was quite surprising and unexpected to find that the agglomerates could be subjected to a pressure sufficient to cause the agglomerate particles to adhere and form a mechanically stable tablet which included a relatively hard outer shell, and yet retain the quick-liquifying characteristics of the agglomerate in the interior of the tablet.

The term "active ingredient" is used herein in a broad sense and encompasses any material which can be carried by or entrained in the agglomerate. For example, an active ingredient can be a pharmaceutical such as an antacid, analgesic or drug; or a flavor, breath sweetner, vitamin, dietary supplement, or nutrient; or the like and combinations thereof. Active ingredients include but are not limited to food acids; insoluble metal and mineral hydroxides, carbonates, oxides, polycarbophils and salts thereof; adsorbates of active drugs on a magnesium trisilicate base and on a magnesium aluminum silicate base.

The agglomerate can be formed from the carbohydrate particles and the water-soluble binder without an active ingredient, and the active ingredient and agglomerate can be mixed to cause the active ingredient to be entrained by and dispersed in the agglomerate. The agglomerate as formed (i.e., without the active ingredient) has a bulk density of from about 40 percent to about 55 percent of the bulk density of the carbohydrate-based particles before they are processed into the agglomerate. The bulk density of the agglomerate itself is relatively low and in the range of from about 0.2 gm/cc to about 0.5 gm/cc (12.5 lbs/ft$^3$ to 31.2 lbs/ft$^3$). A substantial part of the agglomerate consists of voids, i.e., pores or ducts, which provide an extremely large surface area capable of entraining and dispersing substantial quantities of active ingredients, ordinarily about 10 percent to about 50 percent by weight of the finished agglomerate (which includes the entrained active ingredient). The agglomerate and entrained active ingredient have particular utility as a direct compression agglomerate from which tablets according to the invention can be made, particularly chewable tablets which liquify in saliva.

A process for making the carbohydrate-based agglomerate comprises the steps of forming a fluidized bed of the carbohydrate particles, intermittently spraying a solution of the water soluble binder in a droplet size of from about 20 microns to about 100 microns into the fluidized bed so as to cause intimate comingling of solution and carbohydrate particles and adhesion together of carbohydrate particles to form agglomerated particles, drying the particles in the fluidized bed between intermittent sprayings, and continuing spraying and drying until the desired amount of solution has been sprayed into the bed. Thereafter, the agglomerated particles are dried to a desired moisture content or the equilibrium moisture content. The amount of liquid binder solution sprayed corresponds to a binder content in the agglomerate of from about 1 percent to about 10 percent by weight of the agglomerate (excluding active ingredient). The carbohydrate-based agglomerate, and an active ingredient are mixed, preferably in a low shear blender, in the following proportion by weight of the finished agglomerate (including active ingredient):agglomerate, about 50 percent to about 90 percent; active ingredient, from about 10 percent to about 50 percent. A lubricant is also mixed together with the agglomerate and the active ingredient in the proportion of from about 0.4 percent to about 1 percent by weight of the finished agglomerate (including active ingredient). Flavors can also be mixed with the agglomerate and active ingredient.

The agglomerate can, as formed, entrain the active ingredient and other materials such as a lubricant and flavors. In addition, an agglomerate including the entrained active ingredient can be formed by the process described above for the agglomerate formed without an active ingredient, except the active ingredient, is mixed with the carbohydrate particles and a fluidized bed is formed of this mixture. When the agglomerate is formed with an entrained active ingredient, the active ingredient can comprise up to about 75 percent of the weight of the finished agglomerate (including active ingredient). Physical evidence shows that agglomerates formed with an active ingredient have a structure similar to that of agglomerates formed without an active ingredient.

It has been determined that tablets made from carbohydrate particles passing about 50 mesh (particle size less than about 300 microns) and water insoluble active ingredients passing about 300 mesh (particle size less than about 50 microns) liquify quickly and melt in the mouth without perceivable grit upon chewing. (Mesh sizes given herein refer to the U.S. Standard Sieve Series.) Tablets having carbohydrate particle and water-insoluble active ingredient particle sizes greater than about 300 microns and 50 microns, respectively, liquify too slowly in the mouth to provide a quick liquifying, melt-away table. Active ingredients can have a particle size larger than about 50 microns if they are water-soluble, although smaller particle sizes are desired. It has also been determined that the agglomerate particles should pass about 22 mesh (particle size less than about 800 microns) and be retained on about 100 mesh (particle size greater than about 150 microns).

A process for making a tablet from the finished carbohydrate-based agglomerates described above including from about 0.4 percent to about 1.0 percent of a lubricant, comprises compressing the agglomerate particles with entrained active ingredient and lubricant in conventional tablet-forming apparatus to a hardness sufficient to hold the tablet together and substantially destroy the open pore structure of the agglomerate at the surface of the tablet while substantially maintaining the open pore, i.e., large surface area, structure of the agglomerate in the interior of the tablet. Thus, the agglomerate is compressed so that the interior of the tablet retains the essential porous structure and other physical characteristics of the agglomerate which enable it to liquify quickly, while the physical characteristics of the agglomerate are changed primarily at the surface of the tablet.

For the materials described herein, it has been found that tablets compressed to a hardness of from about 6 kp to about 18 kp have an interior which essentially retains the physical structure of the agglomerate. A thinner outer shell is preferred since more force is required to break a tablet with a thicker shell and less material is provided in the interior of a tablet having a thicker shell. Since the thickness of the outer shell has been found to increase with tablet hardness, a preferred range for compression of the agglomerate is to a hardness of from about 6 kp to about 14 kp. Tablets compressed to a hardness in the range of about 6 kp to about 10 kp have been found to have an outer shell believed to be of micron thickness which is sufficient to close off the interior open pore structure of the tablet, and thereby inhibit penetration of liquid through the outer shell into the interior of the tablet, and yet thick enough to provide mechanical strength to the tablet to resist breaking during manufacture and shipping. A tablet compressed to a hardness of from about 6 kp to about 14 kp requires little force to crack, and once the tablet is broken into pieces upon chewing liquifies rapidly in the saliva of the mouth. Tablets compressed at a hardness of from about 14 kp to about 18 kp were found to have interiors in which the agglomerate substantially retained its physical characteristics, but the shell thickness was such that the tablet as a whole was hard and not as easy to chew as were tablets compressed to hardnesses of less than about 14 kp. In addition, at hardnesses of from about 14 kp to about 18 kp, the shell thickness was such that there was perceptively less material in the interior of the tablet with the desirable quick-liquifying characteristics.

Pressures applied to compress the agglomerates into tablets having a hardness of from about 6 kp to about 18 kp were found to be in the order of about one-third the pressures ordinarily used to make tablets.

DESCRIPTION OF THE PREFERRED EMBODIMENTS

The invention is broadly applicable to making a wide variety of tablets including but not limited to, antacid tablets, cough medicine tablets, sore throat tablets, breath freshener tablets, vitamin tablets, calcium tablets, dietary supplement and nutrient tablets, laxative tablets, cold tablets, analgesic tablets, anti-diarrhea tablets, reducing tablets, pain reliever tablets, sleeping tablets, and many prescription and non-prescription drug and pharmaceutical tablets.

Agglomerates according to the invention can be formed by a fluidized bed/agglomeration process in which the particles to be agglomerated are maintained in a gaseous suspension, and binder in a fine spray is applied to the suspended particles to cause them to adhere together and build into agglomerated particles having the open pore, large surface area structure described herein. The suspended carbohydrate particles from which the agglomerates are made pass 50 mesh, while water insoluble active ingredients and lubricants are fine powders, for examle, passing 300 mesh. Other ingredients such as flavors pass 100 mesh. It was found convenient to use commercially available micopulverized powders (−325 mesh, less than 44 micron particle size) for active ingredients such as calcium carbonate and a lubricant such as magnesium stearate. Where desired, these materials were screened to smaller particle sizes.

The binder is applied in a mist-like or atomized spray having a droplet size of afrom about 20 microns to about 100 microns in diameter. The spray is applied intermittently and the bed particles are dried between sprayings while they are continuously maintained suspended and in a fluidized state. Intermittent spraying and drying continues until the required amount of binder solution has been sprayed into the bed. The moisture content of the bed is thereafter reduced, preferably directly to the final desired moisture content or the equilibrium moisture content, and the agglomerated particles are removed from the bed and sized.

Figure 1:
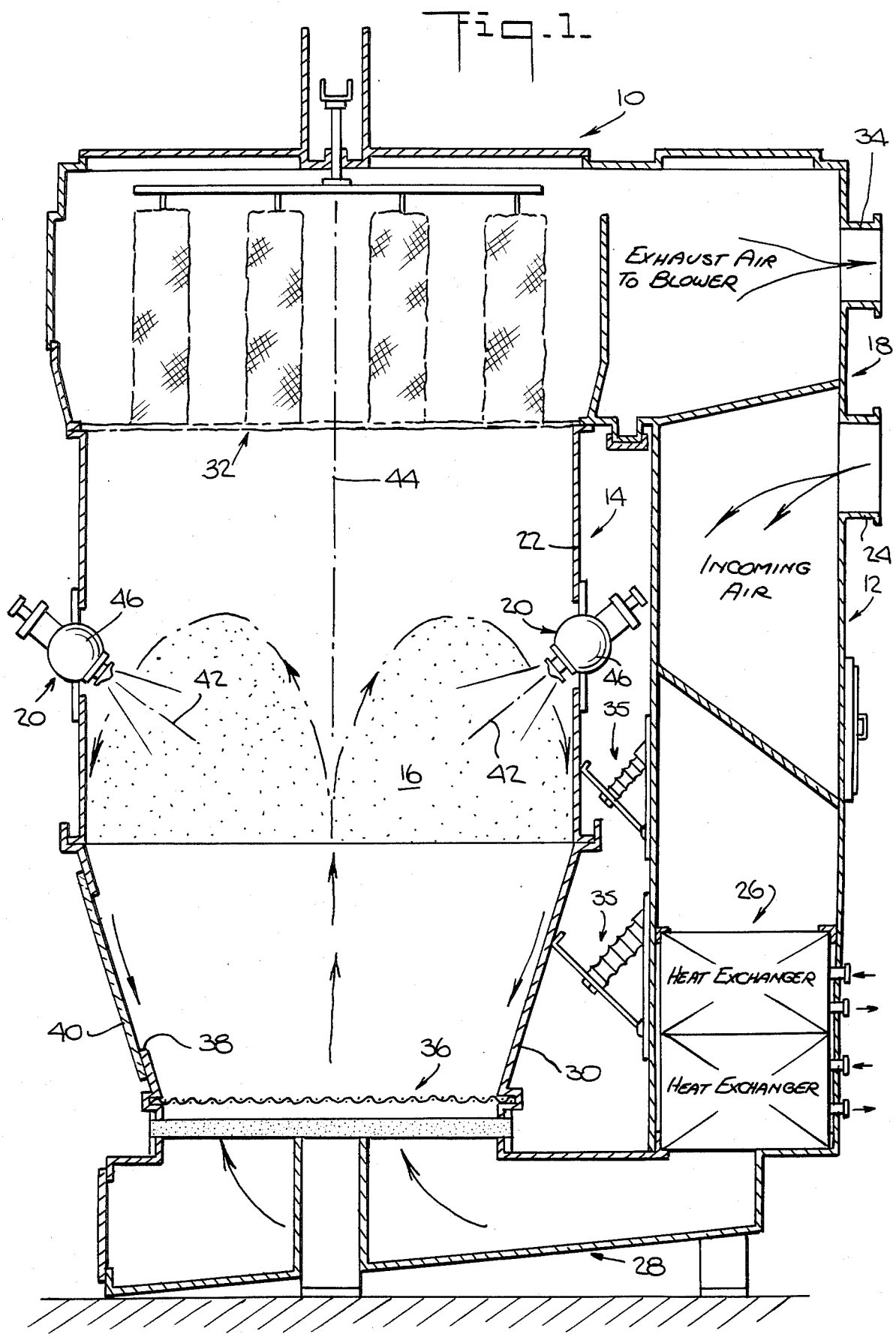
FIG. 1 is a schematic diagram of a fluidized bed spray agglomerator which can be used in accordance with the present invention to form agglomerates according to the present invention.

A spray granulator suitable for making agglomerates of the invention is a Freund Model FL80 pilot-production flow coater. A schematic diagram of the Freund Model FL80 flow coater is depicted in FIG. 1 and designated by reference number 10. The float coater 10 includes a gas intake section 12, a frustro-conical body 14 into which gas from the intake section 12 is drawn to suspend particles 16 therein in a fluidized bed, and an exhaust section 18 for exhausting the gas used to fluidize the bed particles 16. Three binary-type nozzles 20 are equally-spaced about the circumference of an upper cylindrical portion 22 of the body 14, and spray binder solution into the bed particles 16. The binary nozzles 20 utilize gas flows for atomizing the binder solution and for controlling the geometric pattern of the spray.

It is preferred that air can be used as the gas for atomizing the binder solution ("atomizing air"), as the gas for controlling the pattern of the spray ("spray pattern air"), and as the gas for suspending and fluidizing the particles 16 in body 14 ("fluidizing air"). Further description of the flow coater 10 will be made with respect to use of air as these gases, although it should be understood that gases other than air can be used and that for certain gases it may be desirable or necessary to use a closed loop system in which the gas is recycled, or scrubbed before release to the atomosphere.

The gas intake section 12 includes a gas inlet 24 communicated with the atmosphere through which air is drawn into the flow coater 10. Disposed in the gas intake section 12 are heat exchangers 26 through which the incoming air is forced before being introduced into a plenum 28 connected to the conical bottom portion 30 of the flow coater body 14. The heat exchangers 26 can be conventional, and steam/air heat exchangers are preferred. The fluidizing air, after suspending and fluidizing the bed particles 16, is drawn through a micron filter 32 disposed in the exhaust section 18. An exhaust blower (not shown) is communicated with the exhaust outlet 34 of section 18 to draw air through the gas intake section 12, the plenum 28 and the body 14. The entire flow coater 10 is grounded by grounding connectors 35.

The conical bottom portion 30 is a removable bowl having a bottom 36 which supports the particles 16 to be agglomerated while permitting the passage of air therethrough. The bottom 36 can comprise a screen sandwich or other structure capable of supporting powdered material while permitting air to flow through it and lift the powdered material. The bowl 30 includes an opening 38 closed by a transparent cover 40 to permit viewing into the bowl while agglomeration is proceeding.

The binary nozzles 20 are disposed in the cylindrical portion 22 of the body 14 equally spaced about the circumference thereof. The axes 42 of the binary nozzles 20 are disposed at an angle with the horizontal such that the axes intersect at a point generally along the central axis 44 of the body 14 at or below the nozzles. The nozzles 20 are preferably aligned so that the spray ejected therefrom strikes the rising particles perpendicularly. The spherical body portion 46 of the nozzles 20 permits the nozzles to be adjusted and aligned along desired axes in the cylindrical portion 22 of the flow coater body.

Figure 2:
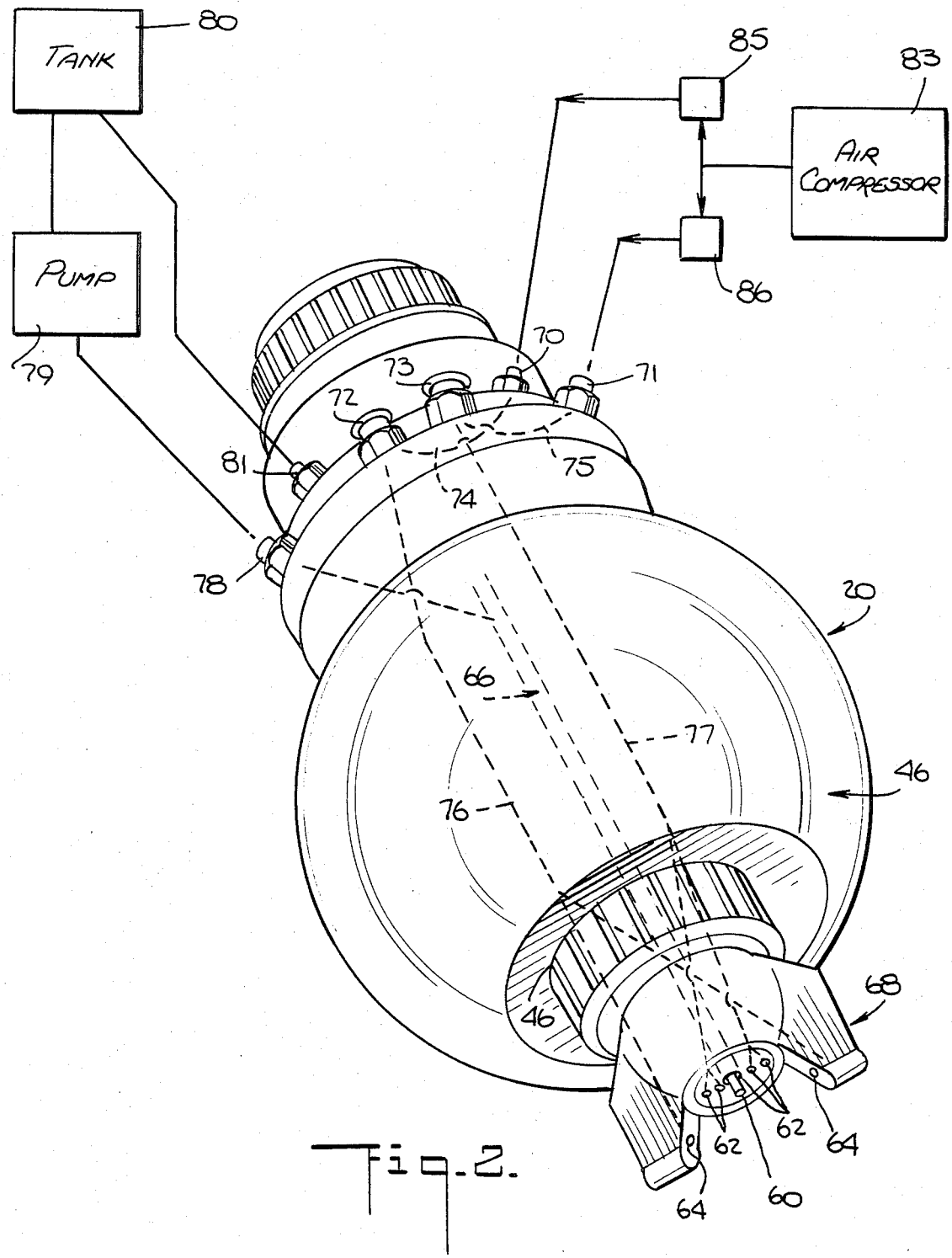
FIG. 2 is an enlarged schematic diagram of a spray nozzle used in the apparatus of FIG. 1 to inject liquid binder solution into the apparatus.

Referring to FIG. 2, each binary nozzle 20 includes openings 60,62 and 64 through which liquid binder, atomizing air and pattern air are respectively expressed from the nozzle. A plurality of openings 62 for the atomizing air are disposed on each side of opening 60 including an annular opening surrounding opening 60, while a single opening 64 for the pattern air is provided on each side of opening 60. Passage 66 through which the liquid binder is delivered to opening 60 projects from the binary nozzle 20. The atomizing air and pattern air are expressed from the binary nozzle through a cap 68 which is threaded to the body 46 of the binary nozzle 20 and is adjustable thereon with respect to the position of the pattern air openings 64. The atomizing air and pattern air are introduced into the binary nozzle 20 through input openings 70,71, respectively, and are communicated with regulators 72, 73, respectively, via passages 74, 75 respectively. The atomizing air and pattern air are delivered to openings 62, 64 from the regulators 72, 73 through passages 76, 77 respectively, extending through the body 46 of the nozzle 20 to the cap 68. Passage 66 for the liquid binder solution is connected via input opening 78 to a fine-toothed, relatively pulseless gear pump 79 which pumps liquid binder solution from a tank 80 to input opening 78 at a constant, pulseless rate, and recycles the solution to the tank 80 from output opening 81 when spraying is discontinued. Input openings 70 and 71 are connected with an air compressor 83 via respective air pressure valves 85, 86, to control the volume of air to output openings 62, 64, respectively. Such valves may form part of the nozzle 20. The pressure and flow rate of the air expressed through openings 62 controls atomization and particle size of the liquid binder solution expressed from opening 60, and the pressure and flow rate of the air expressed through openings 64 control the pattern of the atomized liquid binder solution. The direction of the spray pattern can be controlled by adjustment of the pattern air pressure and/or flow rate, and the atomized particle size can be controlled by adjustment of the atomizing air pressure and flow rate, and the liquid binder pump rate.

The nozzles 20 are commercially available as part of the Freund Model FL80 flow coater, and the construction and operation of the nozzles is understood by those of skill in the art.

The air pressure of the atomizing air and pattern air and the pumping rate of the liquid binder solution are set and controlled in accordance with the particular agglomerate being produced. Also controlled are the quantity of fluidizing air being drawn to fluidize the bed particles, and the heat exchangers 26 to set the temperature of the air introduced into the flow coater.

In operation, the bowl 30 charged with particles to be agglomerated is secured to the body 14 and the exhaust blower is activated to cause air to enter the inlet 14, pass through the heat exchangers 26 and enter into the body 14 after passing through the bowl 30. The incoming air lifts the particles 16 from the bowl and carries them upwardly into the central cylindrical portion 22 of the body 14 with some of the particles rising even higher into the exhaust section where they are trapped by the micron filter 32. A negative pressure is created in the body 14 and the lift created by the exhaust blower is controlled by the volume of air introduced so that the particles are lifted and maintained suspended in a fluidized state in the cylindrical portion 22, and the particles fall along the periphery of the body to be lifted again by the rising air. The particles are thuse continuously lifted, suspended and fall. After the particle motion has reached a somewhat dynamic state of fluidization, the binary nozzles 20 are activated to spray binder solution onto the fluidized particles. The axes of the nozzles are positioned and the geometric spray pattern selected so that the upper part of the cmposite spray of the three nozzles is located at about the middle of the cylindrical portion 22 and strikes the rising particles perpendicularly. The individual spray patterns are preferably generallky fan-like in shape and the width of the individual spray patterns are such that substantially all of the cylindrical portion below and adjacent to the spray nozzles are covered by spray droplets.

The spray nozzles 20 are activated intermittently to spray the fluidized particles 16 with binder solution and the particles are maintained in a fluidized state to effect partial drying of the particles between intermittent sprayings. The micron filter 32 is periodically shaken to return particles it has trapped back to the body 14. After the desired amount of solution has been sprayed by the nozzles 20, the particls are dried to a desired moisture content after which fluidiztion is stopped and the agglomerated particles fall into the bowl 30 which is removed from the flow coater. The agglomerate particles are then sized when they are to be used to make tablets.

For the materials disclosed herein are similar materials, the atomizing air pressure and the pattern air pressure can be in the general range of from 1.5 atm to about 6 atm, the atomizing air flow in the general range of from about 100 m$^3$/hr to about 200 m$^3$/hr, the pattern air flow in the general range of from about 10 m$^3$/hr to about 40 m$^3$/hr, and the liquid binder flow rate in the general range of from about 60 ml/min to about 1,200 ml/min. The following are preferred: atomizing air pressure and pattern air pressure, 4–5 atm; atomizing air flow, 170 m$^3$/hr; pattern air flow, 20 m$^3$/hr; liquid binder flow rate 300 ml/min; air pressure within the flow coater, −0.5 atm; fluidizing air temperature, about 80°.

The different process parameters described above can be set and individually controlled by visual observation and manual setting, or by control systems which semiautomatically or automatically sense and regulate the parameters in accordance with a given control sequence. Process parameters for a particular agglomerate can be programmed into or manually set into such control system. Computerized control systems can be used, if desired, and the construction and operation of control systems for controlling the foregoing process are within the skill of those in the computer and control system arts.

Apparatus other than the Freund FL80 flow coater can be used to produce agglomerates according to the invention. One such apparatus is commercially available as a Freund mini-flow coater. This apparatus includes a single, centrally-disposed nozzle which sprays atomized binder solution into a fluidized bed from above the bed.

Agglomerates have been made in accordance with the process described above using a Freund Model FL80 flow coater. The agglomerates were made from a liquid binder solution of materials described below and carbohydrate particles of the following materials: dextrose monohydrate; dextrose monohydrate and maltodextrin; fructose; fructose and maltodextrin; sucrose; sucrose and maltodextrin; lactose; lactose and maltodextrin; maltose; maltose and maltodextrin; xylose; xylose and maltodextrin. Aqueous solutions of the following materials were used as the liquid binder solution: corn syrup solids; dextrose; sucrose; polyvinylpyrollidone; cooked starch paste; and combinations of the foregoing, any of which may also include maltodextrin. The maltodextrin binder material has a DE of less than about 20% and preferably in the range of from about 5% to about 12%.

The carbohydrate particles passed 50 mesh (particle size less than about 300 microns), and the water-insoluble active ingredients passed 325 mesh (particle size less than about 44 microns). Lubricant particles passed 325 mesh and other materials such as flavors passed 100 mesh. The precise size of the carbohydrate particles is not critical, but agglomerates made from materials having sizes larger than about 50 mesh for the carbohydrate particles and larger than about 300 mesh for the active ingredient do not produce tablets which liquify and melt in the mouth as quickly and as completely as those made with smaller particles. Active ingredients which do not dissolve in the liquid in which a tablet made from the agglomerate is to liquify, e.g., water or saliva, preferably have a particle size of less than about 10 microns. A preferred particle size for such active ingredients is from about 3 microns to about 10 microns. Before being compressed into tablets, the agglomerate particles are sized −22 mesh, +100 mesh (between about 150 microns and about 800 microns). The agglomerate particle size is also not critical and particles in the above range produce tablets having preferred characteristics.

Agglomerates made in accordance with the invention have a honeycomb or zeolite-like structure as described above, in which there are large amounts of voids and surface area. This structure is evident from the following physical characteristics of the agglomerates:

1. The processed agglomerate is free-flowing while the unprocessed carbohydrates generally are not.
2. The processed agglomerates remain free-flowing and do not "lump" in high humidity (e.g., 80%-85% relative humidity), while the unprocessed carbohydrates generally lump and become "mushy".
3. The processed agglomerates liquify in water completely within about 30 seconds with minimal stirring whereas the unprocessed carbohydrates resist liquification and tend to lump even when stirred.
4. The agglomerates processed without an active ingredient can entrain substantial quantities of active ingredients and liquify as described in paragraph 3 above.
5. Agglomerates processed without an active ingredient can absorb up to 25% of the weight of the agglomerate of a low viscosity oil (e.g., mineral oils having a viscosity of about 500 cps) without appearing to be wet and while remaining free flowing.
6. Agglomerates processed without an active ingredient have a bulk density of from about 40% to about 55% of the unprocessed carbohydrate particles, and have a low bulk density of from about 0.2 gm/cc to about 0.5 gm/cc. Agglomerates processed with an active ingredient exhibit similar reductions in bulk density, with the reduction depending on the active ingredient used.
7. The agglomerates as viewed under a microscope has a physical structure similar to that of zeolite and are honeycomb in nature having pores or ducts which were capable of entraining other materials.

Tablets made in accordance with the invention were found to be hard and smooth on the outside but rough, granular and soft on the inside, normally resistant to moisture on the outside and liquid-reactive on the inside. When masticated, the tablets liquified without perceivable grit within about 10 seconds.

Specific examples of agglomerates and tablets made from the agglomerates in accordance with the invention follow. Such Examples are intended to be exemplary and not exhaustive or limiting.

In all of the examples which include maltodextrin, the maltodextrin was Maltrin M-100 (−100 mesh).

In Examples I–XII, the compressed air was supplied to the binary nozzles at about room temperature (e.g., 20-25° C.), and the binder solution was supplied to the binary nozzles at about room temperature. The temperature of the particles charged in the flow coater (which may be at room temperature) was brought up to the bed temperature specified in the Examples by the fluidized air. The pressure in the flow coater in Examples I–XII was about −0.5 atmospheres. The agglomerates were dried to the specified mositure content, although they can be dried to the equilibrium moisture content if desired.

| | | |
|---|---|---|
| Agglomerate Composition | Dextrose Monohydrate | 98.2% w/w |
| | Maltodextrin | 1.8% w/w |
| Agglomerate Moisture Content | 7.5% | |
| Agglomerate Density | 25 lbs. per cubic foot (0.4 gms/cc) | |
| Agglomerate Particle Distribution | Through 22 mesh...100% | |
| | Retained on 88 mesh...100% | |
| Equipment | The Freund Model FL80 pre-production flow coater equipped with three adjustable, peripherally mounted, binary spray nozzles as depicted in FIG. 1. Each nozzle produces a spray mist in a solid, fan-like configuration and is adjusted to inject the liquid binder solution generally perpendicular to the rising bed particles. | |
| Charge Load | 55 kg Dextrose Monohydrate passing 60 mesh | |
| Liquid Binder | 10 liters of 10% w/w maltodextrin water solution | |
| Binder Spray Rate | 300 ml/minute | |

| -continued | |
|---|---|
| Atomizing Air Flow Rate | 170 m³/hr |
| Pattern Air Flow Rate | 20 m³/hr |
| Atomizing Air Pressure | 4 atmospheres |
| Pattern Air Pressure | 4 atmospheres |
| Fluidizing air temperature from heat exchangers | 80° C. |

The agglomerate is made as follows. Charge the flow coater with the dextrose monohydrate; begin fluidization and raise the bed temperature to 35° C. Begin spraying, with intermittent filter shaking and drying, until 10 liters of solution has been delivered through the nozzles onto the bed. Spraying is discontinuous, i.e., spraying followed by drying followed by spraying, to obtain low density particles and to maintain the bed in dynamic motion. To this end, spraying is controlled to prevent overwetting, which could disrupt the bed dynamics and/or produce higher density particles. Dry the product to a moisture content of 7.5% and remove the dextrose monohydrate/maltodextrin agglomerate from the flow coater. Pass the dextrose monohydrate/-maltodextrin agglomerates through a Sweeco sieve bank and crop particles from −22 mesh to +88 mesh.

EXAMPLES II–XII

The agglomerate produced according to Examples II–XII in Table A below, were made as generally described in connection with Example I. In Example II, the pressure of the atomizing air and the pattern air was 5 atmospheres. In Examples III–XII, the pressure of the atomizing air and the pattern air was 4 atmospheres. In Examples II–XII: the liquid binder flow rate was 300 ml/min.; the fluidizing air temperature was 80° C.; the agglomerate density was 0.4 gm/cc; and the agglomerate particle distribution was sized to −22 mesh, +88 mesh.

TABLE A

| | AGGLOMERATE | | CHARGE | | SPRAY | |
|---|---|---|---|---|---|---|
| EXAMPLE | Composition (w/w) | Moisture Content | Particles | Binder (Liters of 10% w/w Maltodextrin in Water) | Atomizing Air Flow Rate $M^3$/hr | Pattern Air Flow Rate $M^3$/hr |
| II | Dextrose Monohydrate 95% Maltodextrin 5% | 7.5% | Dextrose monohydrate (−60 mesh) 52.2 kg Maltodextrin 2.3 kg | 5 | 170 | 20 |
| III | Fructose 95% Maltodextrin 5% | 0.75% | Fructose (−100 mesh) 52.2 kg Maltodextrin 2.3 kg | 5 | 150 | 20 |
| IV | Fructose 98.2% Maltodextrin 1.8% | 0.5% | Fructose (−100 mesh) 55 kg | 10 | 170 | 20 |
| V | Sucrose 98.2% Maltodextrin 1.8% | 0.5% | Sucrose (−100 mesh) 55 kg | 10 | 170 | 20 |
| VI | Sucrose 95% Maltodextrin 5% | 0.75% | Sucrose (−100 mesh) 52.2 kg Maltodextrin 2.3 kg | 5 | 150 | 20 |
| VII | Lactose 98.2% Maltodextrin 1.8% | 0.5% | Lactose (−100 mesh) 55 kg | 10 | 170 | 20 |
| VIII | Lactose 95% Maltodextrin 5% | 0.75% | Lactose (−100 mesh) 52.2 kg Maltodextrin 2.3 kg | 5 | 150 | 20 |
| IX | Maltose 98.2% Maltodextrin 1.8% | 0.5% | Maltose (−100 mesh) 55 kg | 10 | 170 | 20 |
| X | Maltose 95% Maltodextrin 5% | 0.75% | Maltose (−100 mesh) 52.2 kg Maltodextrine 2.3 kg | 5 | 150 | 20 |
| XI | Xylose 98.2% Maltodextrin 1.8% | 0.5% | Xylose (−100 mesh) 55 kg | 10 | 170 | 20 |
| XII | Xylose 95% Maltodextrin 5% | 0.75% | Xylose (−100 mesh) 52.2 kg | 5 | 150 | 20 |

TABLE A-continued

| EXAMPLE | AGGLOMERATE Composition (w/w) | AGGLOMERATE Moisture Content | Particles | CHARGE Binder (Liters of 10% w/w Maltodextrin in Water) | SPRAY Atomizing Air Flow Rate M³/hr | SPRAY Pattern Air Flow Rate M³/hr |
|---|---|---|---|---|---|---|
| | Maltodextrin 2.3 kg | | | | | |

The agglomerates of Examples I–XII exhibited the quick-liquifying characteristics described herein and were suitable for making the inventive tablets described herein. The agglomerates exhibited good flow characteristics, did not lump in high humidity, liquified in water within 30 seconds with minimal stirring and were capable of entraining up to 50% by weight of an active ingredient.

EXAMPLE XIII

In Example XIII, a direct compression agglomerate including an active ingredient was processed directly, as generally described for Example I. The process parameters were as follows:

| | |
|---|---|
| Atomizing air pressure | 4 atm |
| Pattern air pressure | 4 atm |
| Atomizing air flow rate | 170 M³/hr |
| Pattern air flow rate | 20 M³/hr |
| Liquid binder flow rate | 30 ml/min. |
| Fluidizing air temperature | 80° C. |
| Binder solution | 10 liters of 10% w/w maltodextrin in water |

The particles were dried to a moisture content of 4.0% and screened −22 mesh, +88 mesh.

In XIII A–C below, the charge was 60 kg and in XVII D and E, the charge was 300 gm. In XIII A–D, the flavors, the citric acid and the magnesium stearate, were added after the agglomerate was formed. The particle size of the calcium carbonate was about 3 microns to about 10 microns. The magnesium stearate passed −325 mesh and the flavors passed −100 mesh.

| | A % w/w | B % w/w | C % w/w | D % w/w | E % w/w |
|---|---|---|---|---|---|
| Calcium Carbonate | 25.00 | 49.00 | 40.00 | 76.6 | 52.00 |
| Dextrose (−50 mesh) | 71.25 | 48.50 | 57.00 | 22.2 | 43.90 |
| Maltodextrin | 2.54 | 1.29 | 2.79 | — | 1.09 |
| Maltodextrin as 10% Aqueous Solution | 1.21 | 1.21 | 1.21 | 2.2 | 1.21 |
| Flavors | 0.20 | 0.20 | 0.20 | 0.20 | 0.36 |
| Citric Acid | 1.00 | 1.00 | 1.00 | 1.00 | 1.00 |
| Magnesium Stearate | 0.60 | 0.60 | 0.60 | 0.60 | 0.50 |

The agglomerates of Example XIII were observed to have generally the characteristics of the agglomerates of Examples I–XII except that they entrained up to about 76.6% by weight of an active ingredient.

EXAMPLES XIV–XVIII

In Examples XIV through XVIII, the specified active ingredient and lubricants and flavors such as citric acid were milled and weighed, and the specified agglomerate was weighed. These raw materials were then charged, in the pre-weighed quantities falling within the range of about 10% to about 50% by weight of the active ingredient and additives and from about 50% to about 90% by weight of the carbohydrate-based agglomerate, into a low shear blender, e.g., a low intensity ribbon-type mixer or a double trough sigma-type low intensity mixer. The raw materials were mixed in the low shear blender until the active and other ingredients were substantially entrained within the agglomerate. The resulting or finished agglomerate was discharged from the mixer and after validation was ready to be compressed into tablets. The aluminum hydroxide gel and the calcium carbonate had a particle size of from about 3 microns to about 10 microns while the dextromethophan adsorbate passed 100 mesh. The magnesium stearate passed 325 mesh and the flavors passed 100 mesh.

EXAMPLE XIV

| | (a) | (b) |
|---|---|---|
| Dried Aluminum Hydroxide gel (w/w) | 25.0% | 50.0% |
| Magnesium Stearate (w/w) | 0.7% | 0.7% |
| Flavors (w/w) | 0.3% | 0.3% |
| Example I Agglomerate (w/w) | 74.0% | 49.0% |

EXAMPLE XV

| | (a) | (b) |
|---|---|---|
| Magnesium Carbonate (w/w) | 25.0% | 50.0% |
| Magnesium Stearate (w/w) | 0.7% | 0.7% |
| Flavors (w/w) | 0.3% | 0.3% |
| Example II Agglomerate (w/w) | 74.0% | 49.0% |

EXAMPLE XVI

| | (a) | (b) |
|---|---|---|
| Dried Aluminum Hydroxide gel (w/w) | 10.0% | 15.0% |
| Magnesium Carbonate (w/w) | 10.0% | 15.0% |
| Calcium Carbonate (w/w) | 10.0% | 15.0% |
| Magnesium Stearate (w/w) | 0.7% | 0.7% |
| Flavors (w/w) | 0.3% | 0.3% |
| Example II Agglomerate (w/w) | 69.0% | 50.0% |

EXAMPLE XVII

| | (a) | (b) |
|---|---|---|
| 10% Dextromethorphan HB$_R$/Magnesium Trisilicate Adsorbate (w/w) | 6.8% | 16.8% |
| Magnesium Stearate (w/w) | 0.7% | 0.7% |
| Flavors (w/w) | 0.3% | 0.3% |
| Example III Agglomerate (w/w) | 92.2% | 82.2% |

EXAMPLE XVIII

|  | (a) | (b) |
| --- | --- | --- |
| 10% Dextromethorphan HB$_R$/ Magnesium Misilicate Adsorbate (w/w) | 6.8% | 16.8% |
| Magnesium Stearate (w/w) | 0.7% | 0.7% |
| Flavors (w/w) | 0.3% | 0.3% |
| Example II Agglomerate (w/w) | 92.2% | 82.2% |

The agglomerates of Examples XII–XVIII exhibited the quick-liquifying characteristics described herein and were suitable for making the inventive tablets described herein. The agglomerates exhibited good flow characteristics, did not lump in high humidity, and liquified in water at room temperature within 30 seconds with minimal stirring.

EXAMPLES XIX–XXIV

In Examples XIX through XXIV, the finished agglomerate was introduced into standard tabletting apparatus and compressed at reduced pressures over those used conventionally. The pressure was selected to yield tablets having hardnesses of from about 6 kp to about 8 kp and from 12 kp to about 14 kp, which produced tablets having an outer shell in which the large surface area structure of the agglomerate was essentially destroyed and an interior which retained the open-pore structure. In each of Examples XIX through XXIV, the finished agglomerate was compressed into 1.5 gm flat-faced, bevelled-edge tablets. In Examples XIX through XXIII, the calcium carbonate had a particle size of from about 3 microns to about 10 microns and the oyster shell passed 300 mesh. The magnesium sterate and citric acid passed 325 mesh. The flavors passed 100 mesh.

EXAMPLE XIX

|  | (a) | (b) |
| --- | --- | --- |
| Calcium Carbonate (Food Grade) (w/w) | 30.0% | 50.0% |
| Magnesium Stearate (w/w) | 0.7% | 0.7% |
| Flavors (w/w) | 0.3% | 0.3% |
| Example II Agglomerate (w/w) | 69.0% | 49.0% |

EXAMPLE XX

|  | (a) | (b) |
| --- | --- | --- |
| Calcium Carbonate U.S.P. (w/w) | 30.0% | 50.0% |
| Magnesium Stearate (w/w) | 0.7% | 0.7% |
| Flavors (w/w) | 0.3% | 0.3% |
| Example II Agglomerate (w/w) | 69.0% | 49.0% |

EXAMPLE XXI

|  | (a) | (b) |
| --- | --- | --- |
| Calcium Carbonate (w/w) | 30.0% | 50.0% |
| Magnesium Stearate (w/w) | 0.7% | 0.7% |
| Flavors (w/w) | 0.3% | 0.3% |
| Example I Agglomerate (w/w) | 69.0% | 49.0% |

EXAMPLE XXII

|  | (a) | (b) |
| --- | --- | --- |
| Oyster Shell (w/w) | 30.0% | 50.0% |
| Magnesium Stearate (w/w) | 0.7% | 0.6% |
| Flavors (w/w) | 0.3% | 0.4% |
| Example I Agglomerate (w/w) | 69.0% | 49.0% |

EXAMPLE XXIII

|  | (a) | (b) |
| --- | --- | --- |
| Oyster Shell (w/w) | 30.0% | 50.0% |
| Magnesium Stearate (w/w) | 0.7% | 0.6% |
| Flavors (w/w) | 0.3% | 0.4% |
| Example II Agglomerate (w/w) | 69.0% | 49.0% |

EXAMPLE XXIV

The agglomerates of Examples XVIII A-D compressed to a tablet hardness of 7-9 kp.

EXAMPLE XXV (Breath Sweetener)

| Calcium Carbonate (w/w) | 8.0% |
| --- | --- |
| Magnesium Stearate (w/w) | 0.6% |
| Flavors (w/w) | 0.4% |
| Citric Acid (w/w) | 1.0% |
| Example I Agglomerate | 90.0% |
| Tablet Hardness | 6-8 kp |

The tablets of Examples XIX–XXV were found to have the characteristics described herein, i.e., a relatively hard outer shell and a relatively soft interior. The outer shell resisted liquification and unbroken tablets were generally non-hygroscopic. However, once the outer shell was broken and the tablet broken into pieces, as by mastication, it liquified quickly in water, and when masticated, it liquified in the mouth within a few seconds to about 10 seconds into a smooth liquid without perceivable grit.

The examples and the preferred embodiments are not intended to be limiting and the invention applies to agglomerates and tablets other than the antacids, cough medicines and breath sweetener of the examples.

What is claimed is:

1. A tablet comprising an agglomerate, said agglomerate comprising at least about 25% by weight of a carbohydrate-based material including a water-soluble binder, and an active ingredient dispersed in the agglomerate, said carbohydrate-based material comprising from about 1% to about 10% binder by weight, said tablet having an outer surface and an interior, said tablet at said outer surface being harder than in said interior, said tablet being compressed to a hardness sufficient to form a mechanically stable tablet harder at said outer surface, said hardness and the particle size of said carbohydrate based material and of said active ingredient being such as to provide an interior which is rapidly liquifiable into a smooth liquid without perceivable grit when said tablet is masticated and the tablet is broken into pieces and the tablet interior is contacted with saliva.

2. The tablet according to claim 1 wherein the carbohydrate-based material and active ingredients which are water soluable pass about 50 mesh, and active ingredients which are not water soluble pass about 300 mesh.

3. The tablet according to claim 1 wherein the carbohydrate-based material comprises, by weight, from about 90% to about 99% of a carbohydrate selected from the group consisting of dextrose, dextrose monohydrate, maltodextrin, fructose, sucrose, lactose, maltose and xylose, the binder comprises from about 1% to about 10% of a water-soluble binder selected from the group consisting of maltodextrin, corn syrup solids, dextrose, sucrose, polyvinylpyrollidone and cooked starch paste, and the active ingredient comprises up to about 75% by weight of the tablet and is selected from the group consisting of food acids, water insoluble metal and mineral hydroxides, carbonates, oxides and polycarbohphis and salts thereof, and adsorbates of active drugs on magnesium trisilicate and magnesium aluminum silicate bases.

4. The tablet according to claim 1 wherein the hardness is from about 6 kp to about 18 kp.

5. A tablet comprising a compressed agglomerate, the compressed agglomerate comprising at least about 25% by weight of a carbohydrate-based material including a water-soluble binder, and an active ingredient dispersed in the agglomerate, the carbohydrate-based material comprising from about 1% to about 10% binder by weight, the compressed agglomerate forming a mechanically stable tablet having an interior and an outer surface made from the agglomerate, the outer surface being harder than the interior of the tablet, the tablet having a hardness and the particle size of the carbohydrate-based material and of the active ingredient being such as to provide a tablet which is rapidly liquifiable into a smooth liquid without perceivable grit when the tablet is masticated and the tablet is contacted with saliva.

6. The tablet according to claim 5 wherein the carbohydrate-based material and active ingredients which are water soluble pass about 50 mesh, and active ingredients which are not water soluble pass about 300 mesh.

7. The tablet according to claim 5 wherein the carbohydrate-based material comprises, by weight, from about 90% to about 99% of a carbohydrate selected from the group consisting of dextrose, dextrose monohydrate, maltodextrin, fructose, sucrose, lactose, maltose and xylose, and the binder comprises from about 1% to about 10% of a water-soluble binder selected from the group consisting of maltodextrin, corn syrup solids, dextrose, sucrose, polyvinylpyrollidone and cooked starch paste.

8. The tablet according to claim 5 wherein the hardness is from about 6 kp to about 18 kp.

9. The tablet according to claim 5 wherein the active ingredient comprises up to about 75% by weight of the tablet and is selected from the group consisting of food acids, water insoluble metal and mineral hydroxides, carbonates, oxides and polycarbophils and salts thereof, and adsorbates of active drugs on magnesium trisilicate and magnesium aluminum silicate bases.

10. The tablet according to claim 5 wherein the active ingredient comprises up to about 75% by weight of the tablet and is selected from the group consisting of dried aluminum hydroxide gel, magnesium carbonate, calcium carbonate, ground oyster shells, calcium polycarbophil and sodium bicarbonate.

11. The tablet according to claim 7 wherein the active ingredient comprises up to about 75% by weight of the tablet and is selected from the group consisting of food acids, water insoluble metal and mineral hydroxides, carbonates, oxides and polycarbophils and salts thereof, and adsorbates of active drugs on magnesium trisilicate and magnesium aluminum silicate bases.

12. The tablet according to claim 7 wherein the active ingredient comprises up to about 75% by weight of the tablet and is selected from the group consisting of dried aluminum hydroxide gel, magnesium carbonate, calcium carbonate, ground oyster shells, calcium polycarbophil and sodium bicarbonate.

13. A tablet comprising a compressed agglomerate, the compressed agglomerate comprising at least about 25% by weight of a carbohydrate-based material including a water-soluble binder, and an active ingredient dispersed in the agglomerate, the carbohydrate-based material comprising from about 1% to about 10% binder by weight, the agglomerate prior to compression having a large surface area structure, the compressed agglomerate forming a mechanically stable tablet having an interior and an outer surface made from the agglomerate, the tablet at the outer surface being harder than in the interior, the tablet hardness and the particle size of the carbohydrate-based material and of the active ingredient being such that the compressed agglomerate in the table interior substantially retains the large surface area structure of the uncompressed agglomerate, the tablet hardness and the agglomerate being such as to form an outer surface which blocks communication of the large surface area structure of the interior of the table from the exterior of the tablet, the tablet being rapidly liquifiable into a smooth liquid without perceivable grit when the tablet is masticated and the tablet is contacted with saliva.

14. The tablet according to claim 13 wherein the carbohydrate-based material and active ingredients which are water soluble pass about 50 mesh, and active ingredients which are not water soluble pass about 300 mesh.

15. The tablet according to claim 13 wherein the carbohydrate-based material comprises, by weight, from about 90% to about 99% of a carbohydrate selected from the group consisting of dextrose, dextrose monohydrate, maltodextrin, fructose, sucrose, lactose, maltose and xylose, and the binder comprises from about 1% to about 10% of a water-soluble binder selected from the group consisting of maltodextrin, corn syrup solids, dextrose, sucrose, polyvinylpyrollidone and cooked starch paste.

16. The tablet according to claim 13 wherein the tablet hardness is from about 6 kp to about 18 kp.

17. The tablet according to claim 13 wherein the active ingredient comprises up to about 75% by weight of the tablet and is selected from the group consisting of food acids, water insoluble metal and mineral hydroxides, carbonates, oxides and polycarbophils and salts thereof, and adsorbates of active drugs on magnesium trisilicate and magnesium aluminum silicate bases.

18. The tablet according to claim 13 wherein the active ingredient comprises up to about 75% by weight of the tablet and is selected from the group consisting of dried aluminum hydroxide gel, magnesium carbonate, calcium carbonate, ground oyster shells, calcium polycarbophil and sodium bicarbonate.

19. The tablet according to claim 15 wherein the active ingredient comprises up to about 75% by weight of the tablet and is selected from the group consisting of food acids, water insoluble metal and mineral hydroxides, carbonates, oxides and polycarbophils and salts thereof, and adsorbates of active drugs on magnesium trisilicate and magnesium aluminum silicate bases.

20. The tablet according to claim 15 wherein the active ingredient comprises up to about 75% by weight of the tablet and is selected from the group consisting of dried aluminum hydroxide gel, magnesium carbonate, calcium carbonate, ground oyster shells, calcium polycarbophil and sodium bicarbonate.

21. A tablet comprising a compressed agglomerate, the compressed agglomerate comprising at least about 25% by weight of a carbohydrate-based material including a water-soluble binder, and an active ingredient dispersed in the agglomerate, the carbohydrate-based material comprising from about 1% to about 10% binder by weight, the tablet having an interior and an outer surface made from the agglomerate, the tablet at the outer surface being harder than in the interior, the compressed agglomerate tablet having a hardness sufficient to form a mechanically stable tablet, said hardness and the particle size of the carbohydrate-based material and of the active ingredient being such as to provide a tablet which is rapidly liquifiable into a smooth liquid without perceivable grit when the tablet is masticated and the tablet is contacted with saliva.

22. The tablet according to claim 21 wherein the carbohydrate-based material and active ingredients which are water soluble pass about 50 mesh, and active ingredients which are not water soluble pass about 300 mesh.

23. The tablet according to claim 21 wherein the carbohydrate-based material comprises, by weight, from about 90% to about 99% of a carbohydrate selected from the group consisting of dextrose, dextrose monohydrate, maltodextrin, fructose, sucrose, lactose, maltose and xylose, and the binder comprises from about 1% to about 10% of a water-soluble binder selected from the group consisting of maltodextrin, corn syrup solids, dextrose, sucrose, polyvinylpyrollidone and cooked starch paste.

24. The tablet according to claim 21 wherein the tablet hardness is from about 6 kp to about 18 kp.

25. The tablet according to claim 21 wherein the active ingredient comprises up to about 75% by weight of the tablet and is selected from the group consisting of food acids, water insoluble metal and mineral hydroxides, carbonates, oxides, polycarbophils and salts thereof, and adsorbates of active drugs on magnesium trisilicate and magnesium aluminum silicate bases.

26. The tablet according to claim 21 wherein the active ingredient comprises up to about 75% by weight of the tablet and is selected from the group consisting of dried aluminum hydroxide gel, magnesium carbonate, calcium carbonate, ground oyster shells, calcium polycarbophil and sodium bicarbonate.

27. The tablet according to claim 21 wherein the active ingredient comprises up to about 75% by weight of the tablet and is selected from the group consisting of food acids, water insoluble metal and mineral hydroxides, carbonates, oxides and polycarbophils and salts thereof, and adsorbates of active drugs on magnesium trisilicate and magnesium aluminum silicate bases.

28. The tablet according to claim 21 wherein the agglomerate prior to compression has a large surface area structure, the tablet interior substantially retaining the large surface area structure of the uncompressed agglomerate.

29. The tablet according to claim 23 wherein the active ingredient comprises up to about 75% by weight of the tablet and is selected from the group consisting of dried aluminum hydroxide gel, magnesium carbonate, calcium carbonate, ground oyster shells, calcium polycarbophil and sodium bicarbonate.

30. A tablet comprising a directly compressed agglomerate which agglomerate comprises a carbohydrate-based material selected from the group consisting of dextrose, dextrose monohydrate, maltodextrin, fructose, sucrose, lactose, maltose and xylose, a water-soluble binder selected from the group consisting of maltodextrin, corn syrup solids, dextrose, sucrose, polyvinylpyrollidone and cooked starch paste, and an active ingredient, the carbohydrate-based material and the binder combined comprising from at least 25% of the agglomerate and the active ingredient comprising up to about 75% of the agglomerate, the directly compressed agglomerate forming a mechanically stable tablet having an interior and an outer surface made from the agglomerate, the table being harder at the outer surface than in the interior, the tablet having a hardness and the particle size of the carbohydrate-based material, of the binder material and of the active ingredient being such as to provide a tablet which is rapidly liquifiable into a smooth liquid without perceivable grit when the tablet is masticated and the tablet is contacted with saliva.

31. The tablet according to calim 30 wherein the carbohydrate-based material, of the binder material and active ingredients which are water soluble pass about 50 mesh, and active ingredients which are not water soluble pass about 300 mesh.

32. The tablet according to claim 30 wherein the uncompressed agglomerate has a large surface area structure, the tablet interior substantially retaining the large surface area structure of the uncompressed agglomerate while the outer surface of the tablet blocks communication of the large surface area structure of the interior of the tablet from the exterior of the tablet.

33. The tablet according to claim 30 wherein the carbohydrate-based material and the binder comprise, by weight, relative to each other, from about 90% to about 99% carbohydrate-based material and from about 1% to about 10% binder material.

34. The tablet according to claim 30 wherein the active ingredient is selected from the group consisting of food acids, water insoluble metal and mineral hydroxides, carbonates, oxides and polycarbophils and salts thereof, and adsorbates of active drugs on magnesium trisilicate and magnesium aluminum silicate bases.

35. The tablet according to claim 30 wherein the carbohydrate-based material and the binder comprise, by weight, relative to each other, from about 95% to about 99% base material and from about 1% to about 5% binder, said binder consisting of maltodextrin.

36. A tablet made according to a process which comprises:
(a) forming an agglomerate from carbohyrate particles and a binder, said agglomerate having a bulk density of from about 40% to about 55% that of the carbohydrate particles;
(b) mixing the agglomerate of step (a) with an active ingredient to entrain the active ingredient in the agglomerate, the resulting agglomerate comprising at least about 50% agglomerate carbohydrate particles and binder and up to 50% active ingredient; and
(c) directly compressing the agglomerate of step (b) into the tablet, the compressed agglomerate forming a mechanically stable tablet having an interior and an outer surface made from the agglomerate, the outer surface being harder then the interior of the tablet, the tablet having a hardness and the particle size of the carbohydrate particles, of the binder material and of the active ingredient being such as to provide a tablet which is rapidly liquifiable into a smooth liquid without perceivable grit when the tablet is masticated and the tablet is contacted with saliva.

37. The tablet according to claim 36 wherein the agglomerate is directly compressed in the presence of a lubricant.

38. The tablet according to claim 36 wherein the binder is water soluble, the carbohydrate particles and active ingredients which are water soluble and the binder material pass about 50 mesh, and active ingredients which are not water soluble pass about 300 mesh.

39. The tablet according to claim 36 wherein the uncompressed agglomerate has a large surface area structure, the tablet interior substantially retaining the large surface area structure of the uncompressed agglomerate, the outer surface of the tablet blocking communication of the large surface area structure of the interior of the tablet from the exterior of the tablet.

40. The tablet according to claim 36 wherein the carbohydrate particles are selected from the group consisting of dextrose, dextrose monohydrate, maltodextrin, fructose, sucrose, lactose, maltose and xylose, and the binder comprises from about 1% to about 10% of a water soluble binder selected from the group consisting of maltodextrine, corn syrup solids, dextrose, sucrose, polyvinylpyrollidone and cooked starch paste.

41. The tablet according to claim 36 wherein the agglomerate is directly compressed to a tablet hardness of from about 6 kp to about 18 kp.

42. The tablet according to claim 36 wherein the agglomerate of step (a) comprises by weight from about 90% to about 99% carbohydrate particles and from about 1% to about 10% binder.

43. A tablet made according to a process which comprises:
  (a) forming an agglomerate from carbohydrate particles, a binder and an active ingredient, the agglomerate comprising by weight at least about 25% carbohydrate particles and binder and up to about 75% active ingredient; and
  (b) directly compressing the agglomerate into the tablet, the compressed agglomerate forming a mechanically stable tablet having an interior and an outer surface made from the agglomerate, the outer surface being harder than the interior of the tablet, the tablet hardness and the particle size of the carbohydrate particles, of the binder material and of the active ingredient being such as to provide a tablet which is rapidly liquifiable into a smooth liquid without perceivable grit when the tablet is masticated and the tablet is contacted with saliva.

44. The tablet according to claim 43 wherein the agglomerate is directly compressed in the presence of a lubricant.

45. The tablet according to claim 44 wherein the binder is water soluble, the carbohydrate particles and active ingredients which are water soluble and the binder material pass about 50 mesh, and active ingredients which are not water soluble pass about 300 mesh.

46. The tablet according to claim 44 wherein the uncompressed agglomerate has a large surface area structure, the tablet interior substantially retaining the large surface area structure of the uncompressed agglomerate, the outer surface of the tablet blocking communication of the large surface area structure of the interior of the tablet from the exterior of the tablet.

47. The tablet according to claim 44 wherein the carbohydrate particles are selected from the group consisting of dextrose, dextrose monohydrate, maltodextrin, fructose, sucrose, lactose, maltose and xylose, and the binder comprises from about 1% to about 10% of a water soluble binder selected from the group consisting of maltodextrine, corn syrup solids, dextrose, sucrose, polyvinylpyrollidone and cooked starch paste.

48. The tablet according to claim 44 wherein the agglomerate is directly compressed to a tablet hardness of from about 6 kp to about 18 kp.

49. The tablet according to claim 44 wherein the carbohydrate particles and binder comprise by weight relative to each other from about 90% to about 99% carbohydrate particles and from about 1% to about 10% binder.

50. A process for making a carbohydrate-based agglomerate comprising the steps of forming a fluidized bed of carbohydrate particles selected from the group consisting of dextrose, dextrose monohydrate, maltodextrin, fructose, sucrose, lactose, maltose and xylose, spraying an aqueous solution of binder in droplets having a diameter of from about 20 microns to about 100 microns into the fluidized bed, the binder solution comprising a binder selected from the group consisting of maltodextrin, dextrose, sucrose, corn syrup solids, polyvinylpyrollidone and cooked starch paste, intermittently stopping the spraying and drying the sprayed particles while in the fluidized bed, continuing the intermittent spraying until a quantity of binder solution has been sprayed into the fluidized bed such that the carbohydrate particles and the binder from the agglomerate which comprises by weight of the agglomerate from about 90% to about 99% carbohydrate particles and from about 1% to about 10% binder, the agglomerate being capable of being compressed into a mechanically stable tablet having an interior and an outer surface formed from the agglomerate which outer surface is harder than the interior of the tablet, the particle size of the carbohydrate particles and of the binder material from which the agglomerate is made being such that the mechanically stable tablet capable of being formed therefrom is rapidly liquifiable into a smooth liquid without perceivable grit when the tablet is masticated and the tablet is contacted with saliva.

51. The process according to the claim 50 wherein the step of forming a fluidized bed comprises forming a fluidized bed which also includes a quantity of active ingredient to provide an agglomerate comprising by weight of up to about 75% active ingredient.

52. The process according to claim 50 wherein the carbohydrate particles, the binder material and water soluble active ingredients pass about 50 mesh and active ingredients which are not water soluble pass about 300 mesh.

53. The process according to claim 50 wherein the agglomerate is capable of being compressed to form said tablet having a hardness of from about 6 kp to about 18 kp.

54. The process according to claim 50 wherein the uncompressed agglomerate has a large surface area structure, and the tablet which the agglomerate is capable of forming in the interior thereof substantially retains the large surface area structure of the uncompressed agglomerate.

55. A process for producing a tablet comprising the steps of:
(a) making a carbohydrate-based agglomerate according to the process which comprises forming a fluidized bed of carbohydrate particles selected from the group consisting of dextrose, dextrose monohydrate, maltodextrin, fructose, sucrose, lactose, maltose and xylose, spraying an aqueous solution of binder in droplets having a diameter of from about 20 microns to about 100 microns into the fluidized bed, the binder solution comprising a binder selected from the group consisting of maltodextrin, dextrose, sucrose, corn syrup solids, polyvinylpyrollidone and cooked starch paste, intermittently stopping the spraying and drying the sprayed particles while in the fluidized bed, continuing the intermittent spraying until a quantity of binder solution has been sprayed into the fluidized bed such that the carbohydrate particles and the binder in the resulting agglomerate comprise by weight from about 90% to about 99% carbohydrate particles and from about 1% to about 10% binder;
(b) mixing the agglomerate of step (a) and a quantity of active ingredient to provide an agglomerate entraining the active ingredient which comprises by weight up to about 50% active ingredient; and
(c) compressing the agglomerate of step (b) to form a mechanically stable tablet having an interior and an outer surface made from the agglomerate, the tablet at the outer surface being harder than in the interior, the tablet hardness and the particle size of the carbohydrate particles, of the binder material and of the active ingredient being such as to provide a tablet which is rapidly liquifiable into a smooth liquid without perceivable grit when the tablet is masticated and the tablet is contacted with saliva.

56. The process according to claim 55 wherein the agglomerate is compressed in the presence of a lubricant.

57. The process according to claim 56 wherein the carbohydrate particles, the binder material and active ingredients which are water soluble pass about 50 mesh, and active ingredients which are not water soluble pass about 300 mesh.

58. The process according to claim 56 wherein the uncompressed agglomerate of step (a) has a large surface area structure, and the tablet formed according to step (c) in the interior thereof substantially retains the large surface area structure of the agglomerate, the outer surface of the tablet blocking communication of the large surface area structure in the interior of the tablet from the exterior of the tablet.

59. The process according to claim 56 wherein the agglomerate is compressed to a tablet hardness of from about 6 kp to about 18 kp.

60. A process for producing a tablet comprising the steps of:
(a) making a carbohydrate-based agglomerate according to a process which includes forming a fluidized bed of carbohydrate particles selected from the group consisting of dextrose monohydrate, maltodextrin, fructose, sucrose, lactose, maltose and xylose, and an active ingredient, spraying an aqueous solution of a binder in droplets having a diameter of from about 20 microns to about 100 microns into the fluidized bed, the binder solution comprising a binder selected from the group consisting of maltodextrin, dextrose, sucrose, corn syrup solids, polyvinylpyrrolidone and cooked starch paste, the relative quantities of carbohydrate particles, binder and active ingredient being selected to provide an agglomerate comprising by weight at least about 25% carbohydrate particles and binder and up to about 75% active ingredient, intermittently stopping the spraying and drying the sprayed particles while in the fluidized bed, continuing the intermittent spraying until the combined weight of the carbohydrate particles and the binder in the resulting agglomerate is from about 90% to about 99% carbohydrate particles and from about 1% to about 10% binder; and
(b) compressing the agglomerate of step (a) to form a mechanically stable tablet having an interior and an outer surface made from the agglomerate, the tablet at the outer surface being harder than in the interior, the tablet hardness and the particle size of the carbohydrate particles, of the binder material and of the active ingredient being such as to provide a tablet which is rapidly liquifiable into a smooth liquid without perceivable grit when the tablet is masticated and the tablet is contacted with saliva.

61. The process according to claim 60 wherein the agglomerate is compressed in the presence of a lubricant.

62. The process according to claim 61 wherein the carbohydrate particles, the binder material and active ingredients which are water soluble pass about 50 mesh, and active ingredients which are not water soluble pass about 300 mesh.

63. The process according to claim 61 wherein the uncompressed agglomerate of step (a) has a large surface area structure, and the tablet formed according to step (c) in the interior thereof substantially retains the large surface area structure of the uncompressed agglomerate, the outer surface of the tablet blocking communication of the large surface area structure in the interior of the tablet from the exterior of the tablet.

64. The process according to claim 61 wherein the agglomerate is compressed to a tablet hardness of from about 6 kp to about 18 kp.

* * * * *